(12) United States Patent
Hu et al.

(10) Patent No.: US 8,207,221 B2
(45) Date of Patent: Jun. 26, 2012

(54) CRYSTALLINE POLYMORPHS OF A CXC-CHEMOKINE RECEPTOR LIGAND

(75) Inventors: Mengwei Hu, Washington Township, NJ (US); Younong Yu, East Brunswick, NJ (US); Michael P. Dwyer, Scotch Plains, NJ (US); Arthur G. Taveras, Southborough, MA (US); Agnes Kim-Meade, Fanwood, NJ (US); Jianguo Yin, Plainsboro, NJ (US); Xiaoyong Fu, Edison, NJ (US); Timothy L. McAllister, Westfield, NJ (US); Shuyi Zhang, Parsipanny, NJ (US); Kevin Klopfer, Flemington, NJ (US)

(73) Assignee: Schering Corporation, Kenilworth, NJ (US)

( * ) Notice: Subject to any disclaimer, the term of this patent is extended or adjusted under 35 U.S.C. 154(b) by 828 days.

(21) Appl. No.: 12/174,470

(22) Filed: Jul. 16, 2008

(65) Prior Publication Data

US 2008/0279822 A1 Nov. 13, 2008

Related U.S. Application Data

(63) Continuation of application No. 11/045,772, filed on Jan. 28, 2005, now abandoned.

(60) Provisional application No. 60/540,487, filed on Jan. 30, 2004.

(51) Int. Cl.
*A61K 31/341* (2006.01)
*C07D 307/504* (2006.01)
(52) U.S. Cl. ........................ 514/471; 549/494
(58) Field of Classification Search .................. 514/471; 549/494
See application file for complete search history.

(56) References Cited

U.S. PATENT DOCUMENTS 7,071,342 B2 * 7/2006 Yin et al. ...................... 549/494
7,462,740 B2 * 12/2008 Yin et al. ...................... 564/139
7,910,775 B2 * 3/2011 Yin et al. ...................... 564/167
2004/0147559 A1 7/2004 Taveras et al.

FOREIGN PATENT DOCUMENTS

WO WO 02/083624 10/2002
WO WO 03/080053 10/2003

OTHER PUBLICATIONS

Gonsiorek et al. "Pharmacological . . . " J. Pharm. Exp. ther. v.322(2) p. 477-485 (2007).*
Dean "Analytical Chemistry Handbook" p. 10.24-10.26 (1995).*
Ball et al. "Investigation . . . " p. 1-3 from internet (2011).*
Caira, M., "Crystalline Polymorphism of Organic Compounds", Topics in Current Chemistry, 1998, pp. 163-208, vol. 198.
Dean "Analytical chemistry handbook" p. 10.23-10.26 (1995).
Doelker et al., "Crystalline modification . . . " CA 138:209993 (2002).
Doelker et al., "Physicochemical behavior or active . . . " CA 132:325872 (2000).
Jain et al., "Polymorphisom in pharmacy" Indian Drugs 23(g) 315-329 (1986).
Kirk-Othmer Encyclopedia of Chemical Technology, John Wiley & Sons, Inc., pp. 95-147, Article Online Posting Date: Aug. 16, 2002.
Muzaffar et al., "Polymorphism and drug availability", J. Phar. 1(1) 59-66 (1979).
Otsuka et al., "Effect of polymorphic . . . " Chem. Pharm. Bull 47(6) 852-856 (1999).
Polymorphism Wikipedia, the free encyclopedia, p. 1-2 (2006.
Taday et al., "Using terahertz . . . " J. Pharm. Sci. v.92 (4) p. 831-838 (2003).
International Search Report for PCT/US2005/003414; filed Jan. 28, 2005; 4 pages.
PCT International Preliminary Report on Patentability issued May 15, 2006; International Application No. PCT/US2005/003414, filed Jan. 28, 2005.

* cited by examiner

*Primary Examiner* — Celia Chang
(74) *Attorney, Agent, or Firm* — Patricia A Shatynski; Valerie J. Camara (57) ABSTRACT

The present invention relates to four distinct crystalline polymorphs of a monohydrate of Compound A having the following chemical structure:

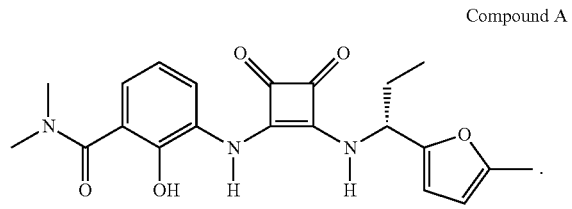

Compound A

These four polymorphic forms, herein referred to as Forms I, II, III and IV are active as a CXC-chemokine receptor ligands. The invention is further directed to formulations, methods of treatment, and processes of synthesis of these polymorphic forms.

5 Claims, 4 Drawing Sheets

CRYSTALLINE POLYMORPHS OF A CXC-CHEMOKINE RECEPTOR LIGAND

CROSS-REFERENCE TO RELATED APPLICATION

The present patent application is a continuation of application Ser. No. 11/045,772, filed Jan. 28, 2005, now abandoned, which claims priority from U.S. Provisional Application No. 60/540,487, filed Jan. 30, 2004.

FIELD OF THE INVENTION

The present invention relates to crystalline polymorphs of a substituted cyclobutenedione compound, pharmaceutical compositions containing the polymorphs, and methods and formulations in treating CXC chemokine-mediated diseases.

BACKGROUND OF THE INVENTION

Chemokines are chemotactic cytokines that are released by a wide variety of cells to attract macrophages, T-cells, eosinophils, basophils, neutrophils and endothelial cells to sites of inflammation and tumor growth. There are two main classes of chemokines, the CXC-chemokines and the CC-chemokines. The class depends on whether the first two cysteines are separated by a single amino acid (CXC-chemokines) or are adjacent (CC-chemokines). The CXC-chemokines include interleukin-8 (IL-8), neutrophil-activating protein-1 (NAP-1), neutrophil-activating protein-2 (NAP-2), GROα, GROβ, GROγ, ENA-78, GCP-2, IP-10, MIG and PF4. CC chemokines include RANTES, MIP-1α, MIP-2β, monocyte chemotactic protein-1 (MCP-1), MCP-2, MCP-3 and eotaxin. Individual members of the chemokine families are known to be bound by at least one chemokine receptor, with CXC-chemokines generally bound by members of the CXCR class of receptors, and CC-chemokines by members of the CCR class of receptors. For example, IL-8 is bound by the CXCR-1 and CXCR-2 receptors.

Since CXC-chemokines promote the accumulation and activation of neutrophils, these chemokines have been implicated in a wide range of acute and chronic inflammatory disorders including psoriasis and rheumatoid arthritis. Baggiolini et al., FEBS Let. 307, 97 (1992); Miller et al., Crit. Rev, Immunol. 12, 17 (1992); Oppenheim et al., Annu. Fev. Immunol. 9, 617 (1991); Seitz et al., J. Clin. Invest. 87, 463 (1991); Miller et al., Am. Rev. Respir. Dis. 146, 427 (1992); Donnely et al., Lancet 341, 643 (1993).

ELRCXC chemokines, including IL-8, GROα, GROβ, GROγ, NAP-2, and ENA-78 (Strieter et al. 1995 JBC 270 p. 27348-57), have also been implicated in the induction of tumor angiogenesis (new blood vessel growth). All of these chemokines are believed to exert their actions by binding to the 7 transmembrane G-protein coupled receptor CXCR2 (also known as IL-8RB), while IL-8 also binds CXCR1 (also known as IL-8RA). Thus, their angiogenic activity is due to their binding to and activation of CXCR2, and possibly CXCR1 for IL-8, expressed on the surface of vascular endothelial cells (ECs) in surrounding vessels.

Many different types of tumors have been shown to produce ELRCXC chemokines and their production has been correlated with a more aggressive phenotype (Inoue et al. 2000 Clin. Cancer Res. 6 p. 2104-2119) and poor prognosis (Yoneda et al. 1998 J. Nat. Cancer Inst. 90 p. 447-454). Chemokines are potent chemotactic factors and the ELRCXC chemokines have been shown to induce EC chemotaxis. Thus, these chemokines probably induce chemotaxis of endothelial cells toward their site of production in the tumor. This may be a critical step in the induction of angiogenesis by the tumor. Inhibitors of CXCR2 or dual inhibitors of CXCR2 and CXCR1 will inhibit the angiogenic activity of the ELRCXC chemokines and therefore block the growth of the tumor. This anti-tumor activity has been demonstrated for antibodies to IL-8 (Arenberg et al. 1996 J. Clin. Invest. 97 p. 2792-2802), ENA-78 (Arenberg et al. 1998 J. Clin. Invest. 102 p. 465-72), and GROα (Haghnegahdar et al. J. Leukoc Biology 2000 67 p. 53-62).

Many tumor cells have also been shown to express CXCR2 and thus tumor cells may also stimulate their own growth when they secrete ELRCXC chemokines. Thus, along with decreasing angiogenesis, inhibitors of CXCR2 may directly inhibit the growth of tumor cells.

Hence, the CXC-chemokine receptors represent promising targets for the development of novel anti-inflammatory and anti-tumor agents.

There remains a need for compounds that are capable of modulating activity at CXC-chemokine receptors. For example, conditions associated with an increase in IL-8 production (which is responsible for chemotaxis of neutrophil and T-cell subsets into the inflammatory site and growth of tumors) would benefit by compounds that are inhibitors of IL-8 receptor binding.

SUMMARY OF THE INVENTION

This invention provides a crystalline polymorph of a monohydrate of Compound A of the formula:

wherein, said polymorph is selected from the group consisting of:
Form I that exhibits a powder x-ray diffraction pattern substantially the same as the pattern shown in FIG. 1;
Form II that exhibits a powder x-ray diffraction pattern substantially the same as the pattern shown in FIG. 2;
Form III that exhibits a powder x-ray diffraction pattern substantially the same as the pattern shown in FIG. 3; and
Form IV that exhibits a powder x-ray diffraction pattern substantially the same as the pattern shown in FIG. 4.

This invention further provides a crystalline polymorph Form I of a monohydrate of Compound A of the formula:

that exhibits a powder x-ray diffraction pattern having characteristic peak locations of 6.612, 8.832, 27.024 and 28.134 degrees 2θ.

In another embodiment, the crystalline polymorph Form I exhibits a powder x-ray diffraction pattern having characteristic peak locations of 6.612, 8.832, 13.268, 17.696, 19.492, 20.003, 27.024 and 28.134 degrees 2θ.

In another embodiment, the crystalline polymorph Form I exhibits a powder x-ray diffraction pattern having characteristic peak locations of 6.612, 8.832, 13.268, 17.696, 17.959, 19.492, 20.003, 20.246, 21.123, 26.580, 27.024 and 28.134 degrees 2θ.

Figure 1:
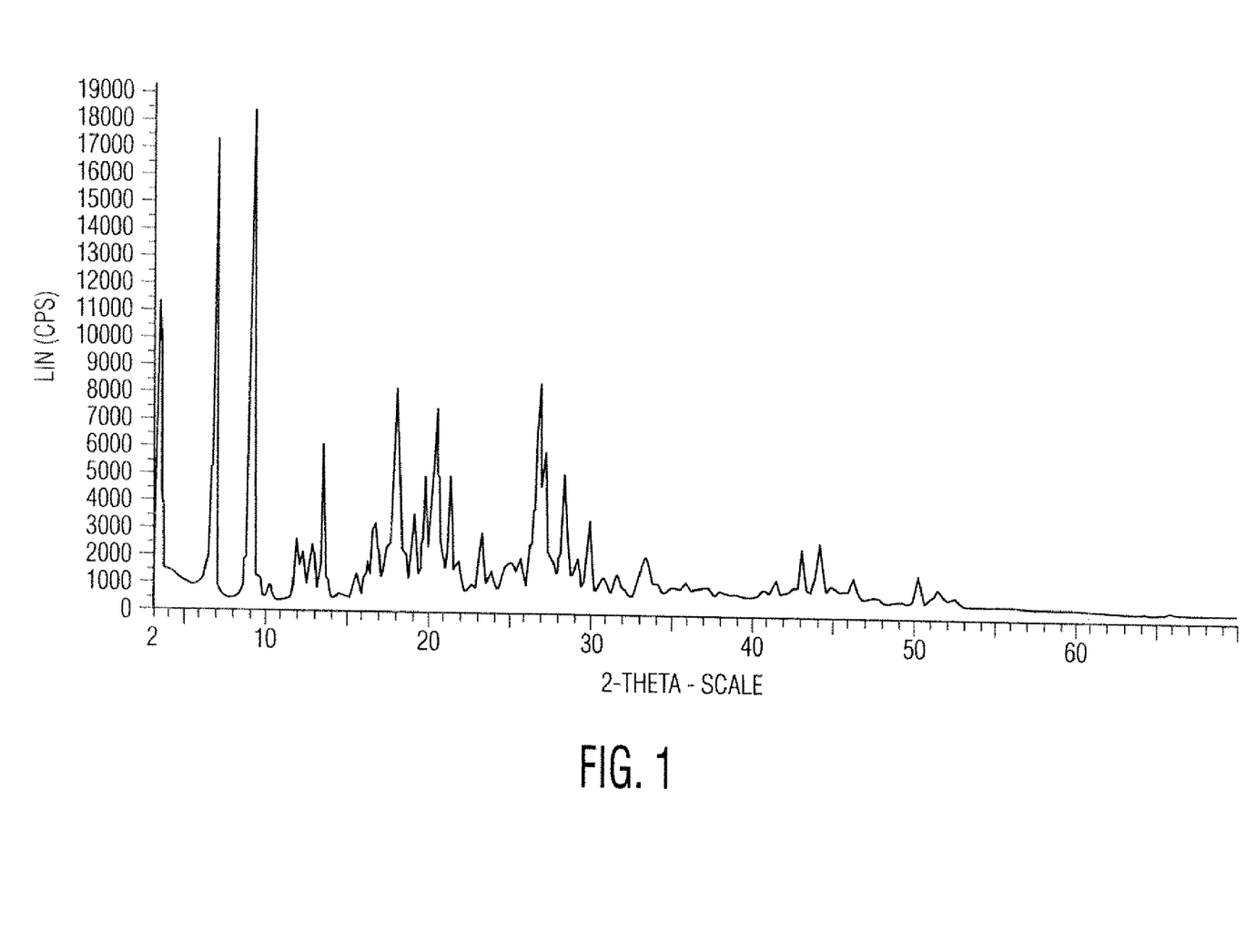
FIG. 1 is a graph of a powder x-ray diffraction (PXRD) pattern of Form I of a monohydrate of Compound A, generated using an X-ray diffractometer. The graph plots the intensity of the peaks as defined by counts per second versus the diffraction angle 2θ in degrees.

In another embodiment, the invention provides the crystalline polymorph Form I that exhibits a powder x-ray diffraction pattern substantially the same as the pattern shown in FIG. 1.

The invention further provides a crystalline polymorph Form II of a monohydrate of Compound A of the formula:

that exhibits a powder x-ray diffraction pattern having characteristic peak locations of 9.328, 13.774, 19.78 and 27.305 degrees 2θ.

In another embodiment, the crystalline polymorph Form II exhibits a powder x-ray diffraction pattern having characteristic peak locations of 9.328, 13.145, 13.774, 15.79, 17.872, 18.748, 19.78 and 27.305 degrees 2θ.

In another embodiment, the crystalline polymorph Form II exhibits a powder x-ray diffraction pattern having characteristic peak locations of 8.742, 9.328, 13.145, 13.774, 15.79, 17.872, 18.748, 19.263, 19.78, 20.166, 26.648 and 27.305 degrees 2θ.

Figure 2:
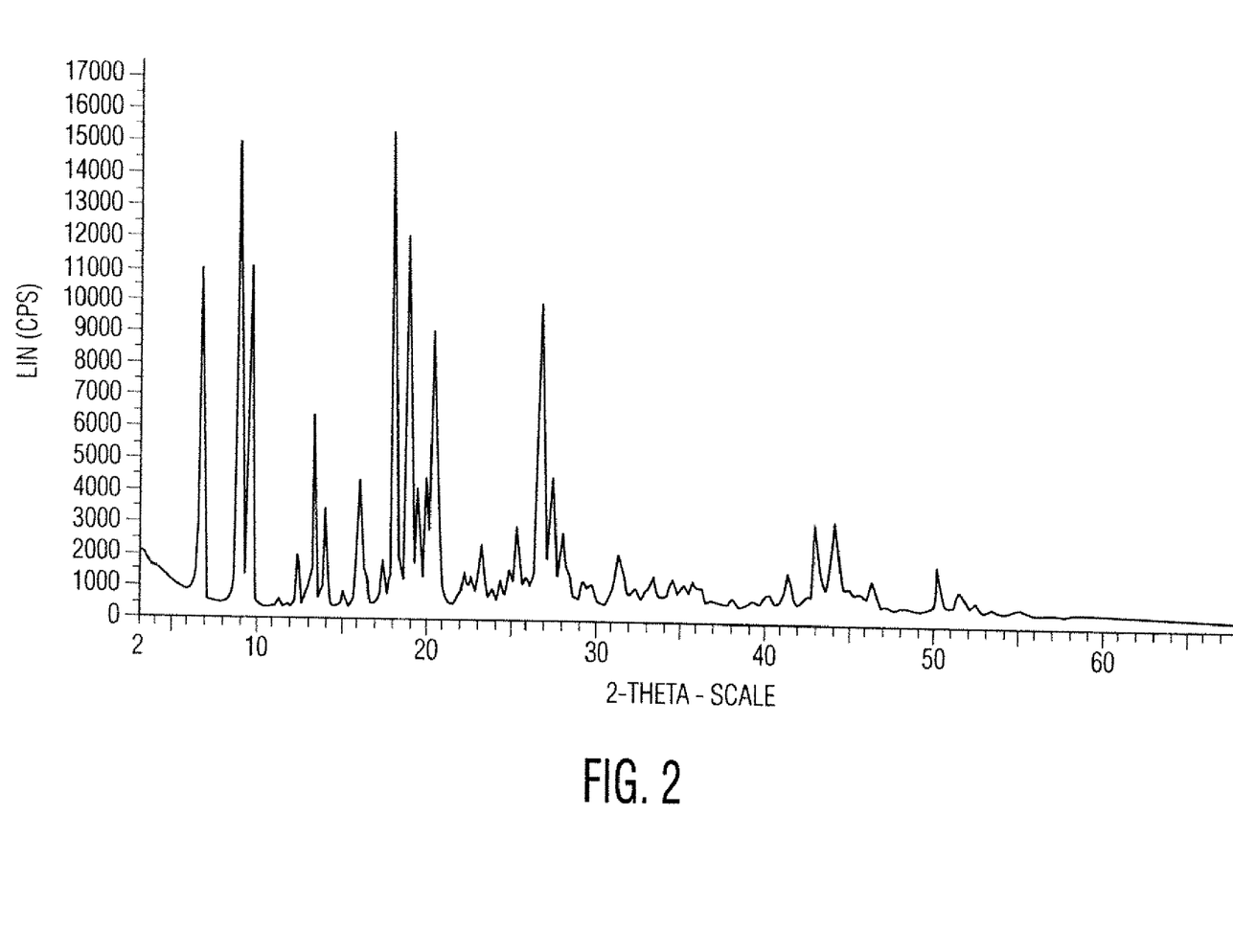
FIG. 2 is a graph of a PXRD pattern of Form II of a monohydrate of Compound A. The graph was generated using an X-ray diffractometer. The graph plots the intensity of the peaks as defined by counts per second versus the diffraction angle 2θ in degrees.

In another embodiment, the invention provides the crystalline polymorph Form II that exhibits a powder x-ray diffraction pattern substantially the same as the pattern shown in FIG. 2.

The invention further provides a crystalline polymorph Form III of a monohydrate of Compound A of the formula:

that exhibits a powder x-ray diffraction pattern having characteristic peak locations of 7.748, 18.349, 23.198 and 23.851 degrees 2θ.

In another embodiment, the crystalline polymorph Form III exhibits a powder ray diffraction pattern having characteristic peak locations of 7.748, 9.632, 14.07, 15.383, 18.349, 23.198, 23.851 and 27.841 degrees 2θ.

In another embodiment, the crystalline polymorph Form III exhibits a powder x-ray diffraction pattern having characteristic peak locations of 7.748, 9.118, 9.632, 14.07, 15.383, 18.349, 18.6, 18.938, 19.383, 23.198, 23.851 and 27.841 degrees 2θ.

Figure 3:
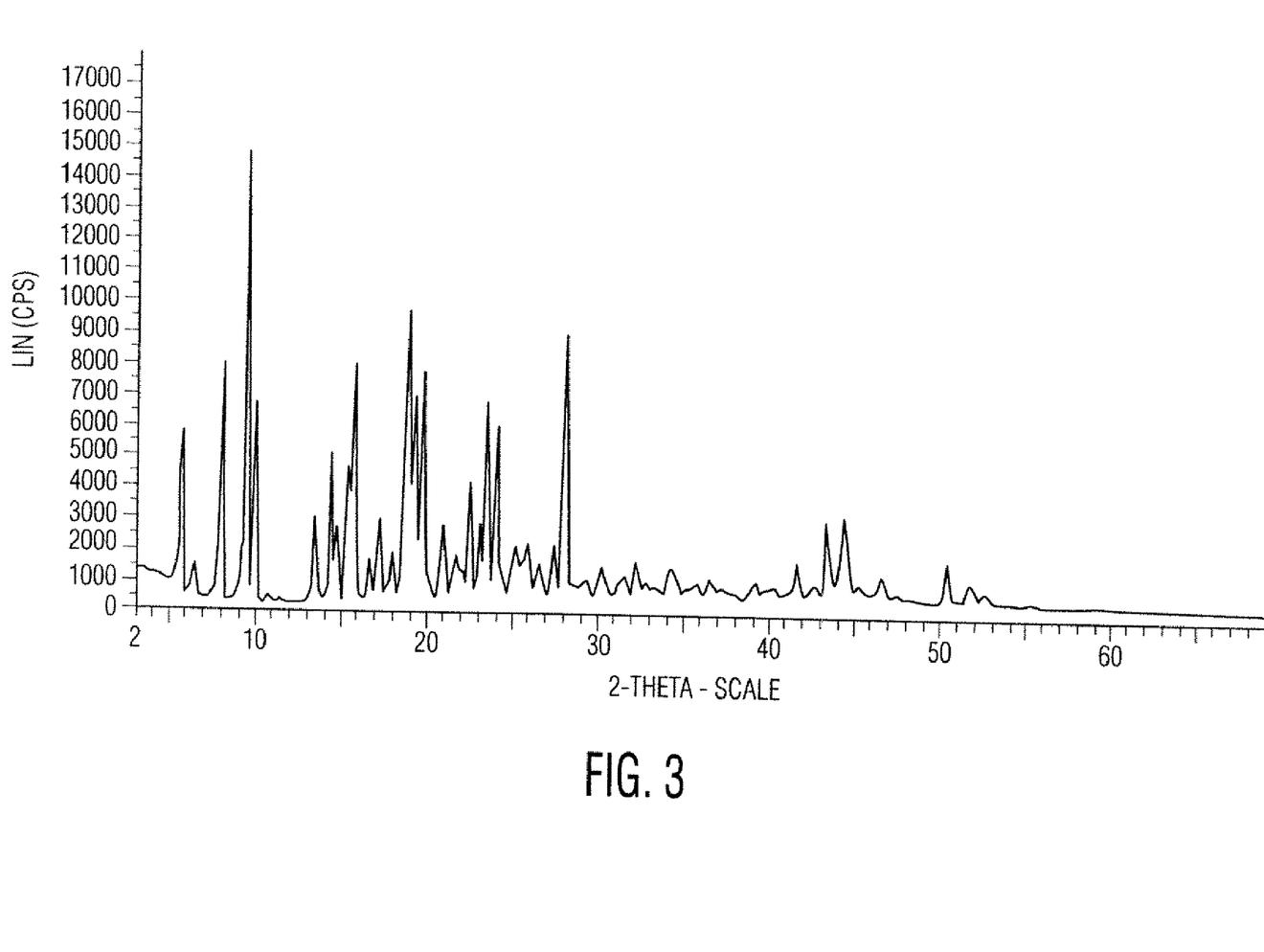
FIG. 3 is a graph of a PXRD pattern of Farm III of a monohydrate of Compound A, generated using an X-ray diffractometer. The graph plots the intensity of the peaks as defined by counts per second versus the diffraction angle 2θ in degrees.

In another embodiment, the invention provides the crystalline polymorph Form III that exhibits a powder x-ray diffraction pattern substantially the same as the pattern shown in FIG. 3.

The invention further provides a crystalline polymorph Form IV of a monohydrate of Compound A of the formula:

that exhibits a powder x-ray diffraction pattern having characteristic peak locations of 11.46, 43.004, 44.097 and 50.107 degrees 2θ.

In another embodiment, the crystalline polymorph Form IV exhibits a powder x-ray diffraction pattern having characteristic peak locations of 11.46, 11.848, 15.643, 16.957, 17.524, 43.004, 44.097 and 50.107 degrees 2θ.

In another embodiment, the crystalline polymorph Form IV exhibits a powder x-ray diffraction pattern having characteristic peak locations of 8.706, 11.46, 11.848, 15.643, 16.957, 17.524, 19.335, 21.079, 26.917, 43.004, 44.097 and 50.107 degrees 2θ.

Figure 4:
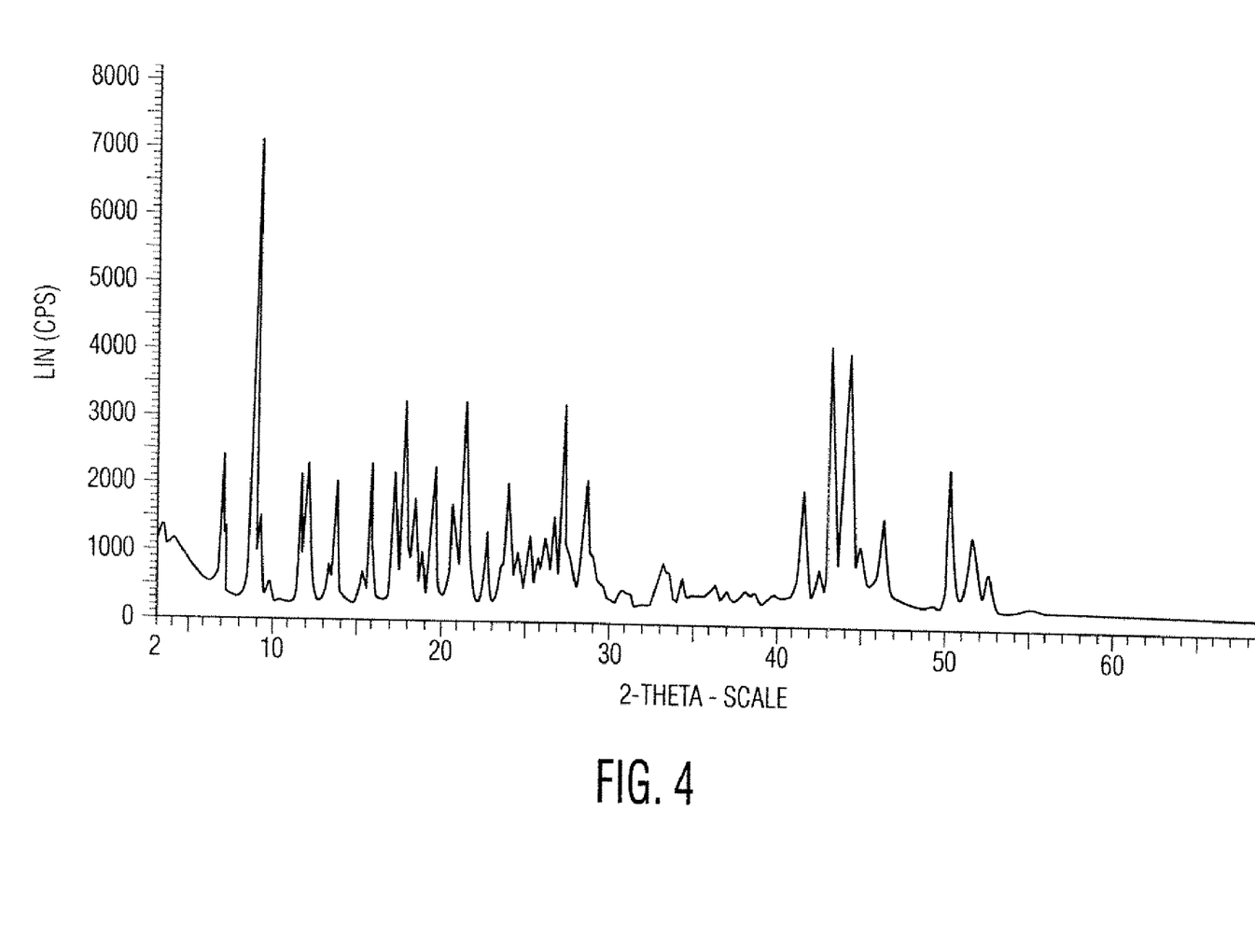
FIG. 4 is a graph of a PXRD pattern of Form IV of a monohydrate of Compound A. The graph was generated using an X-ray diffractometer. The graph plots the intensity of the peaks as defined by counts per second versus the diffraction angle 2θ in degrees.

In another embodiment, the invention provides the crystalline polymorph Form IV that exhibits a powder x-ray diffraction pattern substantially the same as the pattern shown in FIG. 4.

The invention further provides a process for preparing the polymorph Form I from amorphous Compound A:

comprising the steps of:
a) mixing amorphous Compound A at room temperature in a first mixture of an alcohol and water to form a second mixture;
b) adding water dropwise until the second mixture becomes hazy;
c) adding the organic solvent dropwise until the second mixture becomes clear, and
d) allowing the second mixture to stand at room temperature until Form I crystals precipitate.

The invention further provides a crystalline polymorph Form I of the monohydrate of Compound A that is the product of the above process.

In another embodiment, the alcohol is methanol or ethanol.

The invention further provides a process for preparing the polymorph Form II from Form I comprising the step of mixing the Form I material with an organic solvent as a slurry at room temperature until Form II crystals precipitate.

In another embodiment, the organic solvent is methylene chloride or acetone.

The invention further provides a process for preparing the polymorph Form III from Compound A:

comprising the steps of:
a. mixing Compound A at elevated temperature with a first quantity of an organic solvent to form a mixture;
b. adding water portion-wise until precipitate is detected;
c. adding a second quantity of the organic solvent;
d. heating the mixture to about 70° C.; and
e. allowing the mixture to stand at room temperature until Form III crystals precipitate.

The invention further provides a crystalline polymorph Form II of the monohydrate of Compound A that is the product of the above process.

The invention further provides a crystalline polymorph Form III of the monohydrate of Compound A that is the product of the above process.

In another embodiment, the organic solvent is n-propanol.
In another embodiment, the ratio of the first quantity to the second quantity is about 2:1.

The invention further provides a process for preparing the polymorph Form IV from Compound A comprising the step of mixing the Compound A material with acetonitrile as a slurry at room temperature until Form IV crystals precipitate.

The invention further provides a crystalline polymorph Form IV of the monohydrate of Compound A that is the product of the above process.

The invention further provides a process for preparing the polymorph Form IV from Compound A comprising the steps of:
a. mixing Compound A material with a first mixture of n-propanol and water to form a second mixture;
b. agitating said second mixture while heating to about 70° C. until substantially all solids are dissolved;
c. cooling said second mixture to about 60° C.; and
d. agitating said second mixture until Form IV crystals precipitate.

The invention further provides a crystalline polymorph Form IV of the monohydrate of Compound A that is the product of the above process.

In another embodiment, the first mixture comprises n-propanol and water in a ratio of about 1.1:1.

The invention further provides a pharmaceutical composition comprising a crystalline polymorph selected from the group consisting of Form I, Form II, Form III, and Form IV and at least one excipient or carrier.

The invention further provides a purified form of the polymorph Form I.

The invention further provides a purified form of the polymorph Form II.

The invention further provides a purified form of the polymorph Form III.

The invention further provides a purified form of the polymorph Form IV.

The invention further provides a method of treating a chemokine-mediated disease, in a patient in need of such treatment wherein the chemokine binds to a CXCR2 and/or CXCR1 receptor in said patient, comprising administering to said patient an effective amount of at least one polymorph of compound A.

The invention further provides a method of treating a chemokine-mediated disease, in a patient in need of such treatment, wherein the chemokine binds to a CXC receptor in said patient, comprising administering to said patient an effective amount of at least one polymorph of compound A.

The invention further provides a method of treating a chemokine-mediated disease, in a patient in need of such treatment wherein the chemokine is selected from the group consisting of: pain, acute inflammation, chronic inflammation, rheumatoid arthritis, psoriasis, atopic dermatitis, asthma, COPD, adult respiratory disease, arthritis, inflammatory bowel disease, Crohn's disease, ulcerative colitis, septic shock, endotoxic shock, gram negative sepsis, toxic shock syndrome, stroke, ischemia reperfusion injury, renal reperfusion injury, glomerulonephritis, thrombosis, Alzheimer's disease, graft vs. host reaction, allograft rejections, malaria, acute respiratory distress syndrome, delayed type hypersensitivity reaction, atherosclerosis, cerebral ischemia, cardiac ischemia, osteoarthritis, multiple sclerosis, restinosis, angiogenesis, osteoporosis, gingivitis, respiratory viruses, herpes viruses, hepatitis viruses, HIV, Kaposi's sarcoma associated virus, meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute pancreatitis, chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred, corneal neovascularization, polymyositis, vasculitis, acne, gastric ulcers, duodenal ulcers, celiac disease, esophagitis, glossitis, airflow obstruction, airway hyperresponsiveness, bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy, periodontitis, cancer, transplant reperfusion injury, and early transplantation rejection.

The invention further provides a method of treating a chemokine-mediated disease, in a patient in need of such treatment wherein said:

Allograft rejections are selected from the group consisting of acute allograft rejections and chronic allograft rejections, Early transplantation rejection is an acute allograft rejection, Autoimmune deafness is Meniere's disease, Myocarditis is viral myocarditis, Neuropathies are selected from the group consisting of IgA neuropathy, membranous neuropathy and idiopathic neuropathy, Autoimmune diseases are anemias, Vasculitis syndromes are selected from the group consisting of giant cell arteritis, Behcet's disease and Wegener's granulomatosis, and pain is selected from the group consisting of: acute pain, acute inflammatory pain, chronic inflammatory pain, and neuropathic pain, including acute and chronic neuropathic pain.

The invention further provides a method of treating angina in a patient in need of such treatment comprising administering to said patient a therapeutically effective amount of at least one polymorph of Compound A.

The invention further provides a method of treating cancer in a patient in need of such treatment comprising administering to said patient an effective amount of at least one polymorph of Compound A.

The invention further provides the above method of treating cancer in a patient in need of such treatment further comprising the administration of at least one anticancer agent.

The invention further provides the above method of treating cancer in a patient in need of such treatment, wherein said anticancer agent is selected from the group consisting of: alkylating agents, antimetabolites, natural products and their derivatives, hormones, ant-hormones, anti-angiogenic agents and steroids, and synthetics.

The invention further provides a method of inhibiting angiogenesis in a patient in need of such treatment comprising administering to said patient an effective amount of at least one polymorph of Compound A in combination with the administration of an effective amount of at least one anti-angiogenesis compound.

The invention further provides a method of treating a disease selected from the group consisting of: gingivitis, respiratory viruses, herpes viruses, hepatitis viruses, HIV, kaposi's sarcoma associated virus and atherosclerosis, in a patient in need of such treatment, comprising administering to said patient an effective amount of at least one polymorph of Compound A.

The invention further provides a method of treating a chemokine mediated disease wherein the disease is an angiogenic ocular disease.

The invention further provides a method of treating a angiogenic ocular disease wherein said angiogenic ocular disease is selected from the group consisting of: ocular inflammation, retinopathy of prematurity, diabetic retinopathy, macular degeneration with the wet type preferred and corneal neovascularization.

The invention further provides the above method of treating cancer in a patient in need of such treatment, wherein the cancer treated is melanoma, gastric carcinoma, or non-small cell lung carcinoma.

The invention further provides the above method of treating a chemokine mediated disease in a patient in need of such treatment wherein said disease is COPD.

The invention further provides the above method of treating a chemokine mediated disease in a patient in need of such treatment wherein said disease is acute inflammation.

The invention further provides the above method of treating a chemokine mediated disease in a patient in need of such treatment wherein said disease is rheumatoid arthritis.

The invention further provides the above method of treating a chemokine mediated disease in a patient in need of such treatment wherein said disease is acute inflammatory pain.

The invention further provides the above method of treating a chemokine mediated disease in a patient in need of such treatment, wherein said disease is chronic inflammatory pain.

The invention further provides the above method of treating a chemokine mediated disease in a patient in need of such treatment, wherein said disease is neuropathic pain.

The invention further provides a method of treating pain comprising the step of administering to a patient in need of treatment a therapeutically effective amount of at least one polymorph of Compound A having the structure:

The invention further provides the above method of treating pain, wherein said pain is associated with: allodynia, ankylosing spondylitis, appendicitis, autoimmune disorders, bacterial infections, Behcet's syndrome, broken bones, bronchitis, burns, bursitis, cancer including metastatic cancer, candidiasis, cardiovascular conditions, casualgia, chemical injury, childbirth, chronic regional neuropathies, Crohn's disease, colorectal cancer, connective tissue injuries, conjunctivitis, COPD, decreased intracranial pressure, dental procedures, dermatitis, diabetes, diabetic neuropathy, dysesthesia, dysmenorrhea, eczema, emphysema, fever, fibromyalgia, gastric ulcer, gastritis, giant cell arteritis, gingivitis, gout, gouty arthritis, headache, headache pain resulting from lumbar puncture, headaches including migraine headache, herpes simplex virus infections, HIV, Hodgkin's disease, hyperalgesia, hypersensitivity, inflammatory bowel disease, increased intracranial pressure, irritable bowel syndrome, ischemia, juvenile arthritis, kidney stones, lumbar spondylanhrosis, lower back, upper back and lumbrosacral conditions, lumbar spondylarthrosis, menstrual cramps, migraines, minor injuries, multiple sclerosis, myasthenia gravis, myocarditis, muscle strains, musculoskeletal conditions, myocardial ischemia, nephritic syndrome, nerve root avulsion, neuritis, nutritional deficiency, ocular and corneal conditions, ocular photophobia, ophthalmic diseases, osteoarthritis, otic surgery, otitis externa, otitis media, periarteritis nodosa, peripheral neuropathies, phantom limb pain, polymyositis, post-herpetic neuralgia, post-operative/surgical recovery, post-thoracotomy, psoriatic arthritis, pulmonary fibrosis, pulmonary edema, radiculopathy, reactive arthritis, reflex sympathetic dystrophy, retinitis, retinopathies, rheumatic fever, rheumatoid arthritis, sarcoidosis, sciatica, scleroderma, sickle cell anemia, sinus headaches, sinusitis, spinal cord injury, spondyloarthropathies, sprains, stroke, swimmers ear, tendonitis, tension headaches, thalamic syndrome, thrombosis, thyroiditis, toxins, traumatic injury, trigeminal neuralgia, ulcerative colitis, urogenital conditions, uveitis, vaginitis, vascular diseases, vasculitis, viral infections and/or wound healing.

The invention further provides a method of treating pain in a patient in need of such treatment comprising administering to said patient a therapeutically effective amount of at least one polymorph of Compound A and administering to said patient a therapeutically effective amount of at least one medicament selected from the group consisting of NSAIDs, COXIB inhibitors, anti-depressants, anti-convulsants, anti-TNFα antibodies and TNFα antagonists.

The invention further provides the above method of treating pain, wherein said polymorph is administered as a pharmaceutical composition.

The invention further provides the above method for treating pain, wherein said medicament comprises at least one NSAID.

The invention further provides the above method for treating pain, wherein said medicament comprises at least one COXIB inhibitor.

The invention further provides the above method for treating pain, wherein said medicament comprises at least one anti-depressant.

The invention further provides the above method for treating pain, wherein said medicament comprises at least one anti-convulsant.

The invention further provides the above method for treating pain, wherein said medicament comprises at least one anti-TNFα antibody.

The invention further provides the above method for treating pain, wherein said medicament comprises at least one TNFα antagonist.

The invention further provides the above method for treating pain, wherein said NSAID is selected from the group consisting of: piroxicam, ketoprofen, naproxen, indomethacin, and ibuprofen.

The invention further provides the above method for treating pain, wherein said COXIB inhibitor is selected from the group consisting of: rofecoxib, celecoxib, etoricoxib, valdecoxib and melotican.

The invention further provides the above method for treating pain, wherein said anti-depressant is selected from the group consisting of: amitriptyline and nortriptyline.

The invention further provides the above method for treating pain, wherein said anti-convulsant is selected from the group consisting of: gabapentin, carbamazepine, pregabalin, and lamotrigine.

The invention further provides the above method for treating pain, wherein said anti-TNFα antibody is selected from the group consisting of: infliximab and adalimumab.

The invention further provides the above method for treating pain, wherein said TNFα antagonist is selected from the group consisting of: etanercept, p38 kinase inhibitors, and TNF receptor fusion proteins.

The invention further provides the above method for treating pain, wherein said pain is acute pain.

The invention further provides the above method for treating pain, wherein said pain is neuropathic pain.

The invention further provides the above method for treating pain, wherein said pain is acute inflammatory pain.

The invention further provides the above method for treating pain, wherein said pain is chronic.

The invention further provides a method of treating a chemokine mediated disease or condition in a patient in need of such treatment comprising administering to said patient at least one polymorph of Compound A in combination with at least one other medicament useful for the treatment of chemokine mediated diseases.

The invention further provides a method of treating a chemokine mediated disease or condition in a patient in need of such treatment comprising administering to said patient at least one polymorph of Compound A in combination with at least one other medicament selected from the group consisting of:
  disease modifying antirheumatic drugs;
  nonsteroidal anitinflammatory drugs;
  COX-2 selective inhibitors;
  COX-1 inhibitors;
  immunosuppressives;
  steroids;
  biological response modifiers; and
  other anti-inflammatory agents or therapeutics useful for the treatment of chemokine mediated diseases.

The invention further provides the above method wherein the chemokine mediated disease or condition is pain.

The invention further provides a method of treating a pulmonary disease in a patient in need of such treatment, comprising administering to said patient a therapeutically effective amount of at least one polymorph of Compound A, in combination with at least one compound selected from the group consisting of: glucocorticoids, 5-lipoxygenase inhibitors, β-2 adrenoceptor agonists, muscarinic M1 antagonists, muscarinic M3 antagonists, muscarinic M2 agonists, NK3 antagonists, LTB4 antagonists, cysteinyl leukotriene antagonists, bronchodilators, PDE4 inhibitors, PDE inhibitors, elastase inhibitors, MMP inhibitors, phospholipase A2 inhibitors, phospholipase D inhibitors, histamine H1 antagonists, histamine H3 antagonists, dopamine agonists, adenosine A2 agonists, NK1 and NK2 antagonists, GABA-b agonists, nociceptin agonists, expectorants, mucolytic agents, decongestants, antioxidants, anti-IL-8 anti-bodies, anti-IL-5 antibodies, anti-IgE antibodies, anti-TNF antibodies, IL-10, adhesion molecule inhibitors, and growth hormones. The invention further provides a method of treating multiple sclerosis in a patient in need of such treatment comprising administering to said patient a therapeutically effective amount of at least one polymorph of Compound A in combination with at least one compound selected from the group consisting of glatiramer acetate, glucocorticoids, methotrexate, azothioprine, mitoxantrone, chemokine inhibitors, and CB2-selective agents.

The invention further provides a method of treating multiple sclerosis in a patient in need of such treatment comprising administering to said patient a therapeutically effective amount of at least one polymorph of Compound A in combination with at least one compound selected from the group consisting of: methotrexate, cyclosporin, leflunimide, sulfasalazine, β-methasone, β-interferon, glatiramer acetate, and prednisone.

The invention further provides a method of treating rheumatoid arthritis in a patient in need of such treatment comprising administering to said patient a therapeutically effective amount of at least one polymorph of Compouind A.

The invention further provides a method of treating rheumatoid arthritis in a patient in need of such treatment comprising administering to said patient a therapeutically effective amount of at least one polymorph of Compound A in combination with at least one compound selected from the group consisting of COX-2 inhibitors, COX inhibitors, immunosuppressives, steroids, PDE IV inhibitors, anti-TNF-α compounds, MMP inhibitors, glucocorticoids, chemokine inhibitors, CB2-selective inhibitors, and other classes of compounds indicated for the treatment of rheumatoid arthritis.

The invention further provides a method of treating stroke and cardiac reperfusion injury in a patient in need of such treatment comprising administering to said patient a therapeutically effective amount of at least one polymorph of Compound A in combination with at least one compound selected from the group consisting of thrombolitics, anti-platelet agents, antagonists, anticoagulants, and other compounds indicated for the treatment of rheumatoid arthritis.

The invention further provides a method of treating stroke and cardiac reperfusion injury in a patient in need of such treatment comprising administering to said patient a therapeutically effective amount of at least one polymorph of Compound A in combination with at least one compound selected from the group consisting of tenecteplase, TPA, alteplase, abciximab, eftiifbatide, and heparin.

The invention further provides a method of treating psoriasis in a patient in need of such treatment, comprising administering to said patient a therapeutically effective amount of at least one polymorph of Compound A in combination with at least one compound selected from the group consisting of immunosuppressives, steroids, and anti-TNF-α compounds.

The invention further provides a method of treating COPD in a patient in need of such treatment, comprising administering to said patient a therapeutically effective amount of at least one polymorph of Compound A.

The invention further provides a method of treating arthritis in a patient in need of such treatment, comprising administering to said patient a therapeutically effective amount of at least one polymorph of Compound A.

The invention further provides a method of treating osteoarthritis in a patient in need of such treatment, comprising administering to said patient a therapeutically effective amount of at least one polymorph of Compound A.

DETAILED DESCRIPTION

Compound A is disclosed in WO 02/083624 as Examples 360.31 and 405, which reflect the following chemical structure:

Compound A

Anhydrous Compound A is particularly active as a CXC-chemokine receptor ligand. A monohydrate form of Compound A was found to have substantially similar activity. Four distinct crystalline polymorphs of a monohydrate of Compound A were found to exist. These four forms are herein referred to as Forms I, II, III and IV. Each of the four polymorphs is neutral, i.e., in neither ionic nor salt form. The four crystalline forms can be referred to as polymorphs. Since the intended use of this compound is as a therapeutically active pharmaceutical agent, the most stable pharmaceutically acceptable forms of the monohydrate of Compound A will be of great interest.

Polymorphism can be characterized as the ability of a compound to crystallize into different crystal forms, while maintaining the same chemical formula. A crystalline polymorph of a given drug substance is chemically identical to any other crystalline polymorph of that drug substance in containing the same atoms bonded to one another in the same way, but differs in its crystal forms, which can affect one or more physical properties, such as stability, solubility, melting point, bulk density, flow properties, bioavailability, etc.

As used throughout the specification, the following terms, unless otherwise indicated, shall be understood to have the following meanings:

"Patient" includes both human and other animals.

"Mammal" includes humans and other mammalian animals.

"Polymorph" means a crystalline form of a substance that is distinct from another crystalline form but that shares the same chemical formula.

"Inventive polymorph" means any of the four crystalline polymorphs Forms I-IV of the monohydrate of Compound A, and is not limited to a single polymorph but can include more than one form.

"Alcohol" means an organic compound containing a hydroxyl group (—OH).

"Nitrile" means an organic compound containing a —C≡N group.

"Excipient" means an essentially inert substance used as a diluent or to give form or consistency to a formulation.

"Effective" or "therapeutically effective" is meant to describe a polymorph of a compound or a composition of the present invention effective as a chemokine receptor ligand and thus producing the desired therapeutic, ameliorative, inhibitory or preventative effect. "Effective amount" or "therapeutically effective amount" is meant to describe an amount of polymorph or a composition of the present invention effective as a chemokine receptor ligand and thus producing the desired therapeutic, ameliorative, inhibitory or preventative effect.

Sample Preparation

Forms I-IV of Compound A were analyzed as a dry powder for powder x-ray diffraction ("PXRD") analyses. Forms I, II and III were analyzed without first being micronized. Form IV was analyzed after micronization.

A micronizer was used to grind and classify the Form IV material. The micronizer grinds and classifies the Compound A material in a single shallow chamber. Filtered nitrogen is introduced through peripheral jets. These jets are spaced at regular intervals around the periphery of the grinding chamber. During operation, a high-speed vortex is generated, and the Compound A material is injected into the vortex near the peripheral wall. Strong velocity gradients near the jets cause the suspended particles to collide and reduce one another by impact. Heavier oversized particles are held in the grinding area by centrifugal force. The rate of feed and the grinding gas pressure are the main factors that control the output particle size. The grinding gas exits through an outlet at the top center of the chamber and draws the micronized product with it into the collection bag. The Compound A material is collected in double-polyethylene-bag-lined drums. The batch was micronized at a feed rate of 100 g/min and a mill pressure of 40 psig on a 4 inch micronizer.

The samples were analyzed with minimal preparation to prevent any form changes. The samples were lightly rubbed to insure that particles were not agglomerated. No solvents, drying or other preparation steps were used for these analyses. The PXRD data can uniquely identify the polymorphic forms.

Powder X-Ray Diffraction

The Bruker D8 diffractometer (manufactured in 2002) was used in the powder x-ray powder diffraction studies. It has a parallel optic configuration with a GÖBEL beam focusing mirror and a Position Sensitive Detector ("PSD") equipped with a fixed radial soller slit was used with an Anton Paar TTK450 temperature stage. The radiation source is copper (K$\alpha$). The divergence slits are fixed at 0.6 mm. The sample holder was a top-loading brass block. PSD fast scan was used to scan from 3.0° to 69.9°. Specimens were loaded onto the sample holder and leveled with a glass microscope slide. The sample chamber temperature was set at 30° C., under ambient humidity and not purged with nitrogen and not under vacuum. Instrument calibration was verified using mica standards. During scanning, the step size was 0.013 degrees over step durations of 2 seconds. Data analysis was accomplished using EVA analysis software, version 7.0.0.1, supplied by Bruker® written by SOCABIM®. The data were not smoothed by the software while the peak search was performed with a threshold of 3.

Using the methods and equipment described above, Forms I-IV of Compound A were subjected to PXRD analysis. PXRD patterns were generated and are displayed in FIGS. 1-4. The intensity of the peaks (y-axis is in counts per second) is plotted vesus the 2θ angle (x-axis is in degrees 2θ). In addition, the data were plotted with detector counts normalized for the collection time per step versus the 2θ angle. Peak locations (on the 2θ X-axis) consistent with these profiles are displayed in Table 1. The locations of these PXRD peaks are characteristic of crystalline polymorphs of Forms I-IV of Compound A.

TABLE 1

PXRD Peak Positions for Forms I-IV of Compound A

| Form I | | Form II | | Form III | | Form IV | |
|---|---|---|---|---|---|---|---|
| Peak Location (deg. 2θ) | Intensity (Cps) | Peak Location (deg. 2θ) | Intensity (Cps) | Peak Location (deg. 2θ) | Intensity (Cps) | Peak Location (deg. 2θ) | Intensity (Cps) |
| 3.280 | 11328 | 3.205 | 2020 | 3.287 | 1384 | 3.35 | 1359 |
| 3.832 | 1484 | 6.54 | 10968 | 5.52 | 5845 | 3.971 | 1154 |
| 6.612 | 17385 | 8.742 | 14922 | 6.258 | 1564 | 6.8 | 2404 |
| 8.832 | 18353 | 9.328 | 11006 | 7.748 | 7923 | 8.706 | 7071 |
| 9.345 | 1230 | 10.97 | 584 | 9.118 | 14807 | 9.067 | 1491 |
| 9.983 | 883 | 11.471 | 392 | 9.632 | 6748 | 9.616 | 512 |
| 11.642 | 2643 | 12.101 | 1960 | 10.452 | 483 | 11.46 | 2128 |
| 12.018 | 2208 | 12.543 | 769 | 11.081 | 383 | 11.848 | 2298 |
| 12.551 | 2328 | 12.822 | 1350 | 13.145 | 2996 | 13.158 | 783 |
| 13.268 | 6017 | 13.145 | 6355 | 14.07 | 5081 | 13.545 | 2022 |
| 14.195 | 665 | 13.774 | 3441 | 14.384 | 2785 | 14.014 | 313 |
| 15.232 | 1331 | 14.768 | 817 | 15.083 | 4755 | 15.15 | 678 |
| 15.921 | 1820 | 15.79 | 4271 | 15.383 | 7925 | 15.643 | 2288 |
| 16.370 | 3250 | 16.104 | 1506 | 16.376 | 1706 | 16.957 | 2166 |
| 17.161 | 2379 | 17.13 | 1800 | 16.931 | 3003 | 17.524 | 3268 |
| 17.696 | 8306 | 17.872 | 15217 | 17.684 | 1884 | 18.114 | 1778 |
| 17.959 | 4931 | 18.748 | 12033 | 18.349 | 6974 | 18.623 | 1000 |
| 18.254 | 2255 | 19.263 | 4102 | 18.6 | 9640 | 19.335 | 2266 |
| 18.852 | 3577 | 19.78 | 4396 | 18.938 | 7057 | 20.407 | 1715 |
| 19.492 | 4935 | 20.166 | 8994 | 19.383 | 7682 | 21.079 | 3288 |
| 20.003 | 5410 | 20.507 | 2201 | 20.645 | 2861 | 21.569 | 741 |
| 20.246 | 7443 | 21.675 | 787 | 21.415 | 1858 | 22.387 | 1299 |
| 21.123 | 4989 | 22.023 | 1467 | 21.667 | 1475 | 23.348 | 810 |
| 21.581 | 1856 | 22.42 | 1394 | 22.187 | 4174 | 23.687 | 2040 |
| 22.473 | 1070 | 23.078 | 2332 | 22.796 | 2881 | 24.335 | 1030 |
| 23.063 | 2946 | 23.705 | 965 | 23.198 | 6709 | 24.946 | 1266 |
| 23.687 | 1548 | 24.229 | 1215 | 23.851 | 5987 | 25.425 | 926 |
| 24.904 | 1862 | 24.761 | 1491 | 24.883 | 2118 | 25.854 | 1240 |
| 25.438 | 1979 | 25.209 | 2937 | 25.336 | 1780 | 26.357 | 1546 |
| 26.580 | 8497 | 25.741 | 1402 | 25.682 | 2210 | 26.917 | 3247 |
| 27.024 | 5901 | 26.648 | 9917 | 26.221 | 1613 | 27.29 | 1040 |
| 27.409 | 2024 | 27.305 | 4457 | 27.139 | 2199 | 28.307 | 2084 |
| 28.134 | 5093 | 27.941 | 2750 | 27.841 | 8966 | 29.028 | 625 |
| 28.931 | 2049 | 28.312 | 1354 | 29.031 | 1159 | 29.75 | 389 |
| 29.731 | 3445 | 29.182 | 1217 | 30.017 | 1604 | 30.429 | 512 |

TABLE 1-continued

PXRD Peak Positions for Forms I-IV of Compound A

| Form I | | Form II | | Form III | | Form IV | |
|---|---|---|---|---|---|---|---|
| Peak Location (deg. 2θ) | Intensity (Cps) | Peak Location (deg. 2θ) | Intensity (Cps) | Peak Location (deg. 2θ) | Intensity (Cps) | Peak Location (deg. 2θ) | Intensity (Cps) |
| 30.637 | 1362 | 29.579 | 1151 | 30.931 | 1046 | 30.858 | 415 |
| 31.449 | 1482 | 31.253 | 2112 | 31.253 | 1276 | 32.883 | 902 |
| 31.829 | 997 | 32.286 | 1047 | 31.926 | 1704 | 33.242 | 763 |
| 33.156 | 2063 | 32.92 | 994 | 32.525 | 1155 | 34.091 | 663 |
| 33.855 | 1204 | 33.296 | 1435 | 33.926 | 1485 | 36.114 | 607 |
| 34.798 | 1020 | 34.475 | 1408 | 34.828 | 881 | 36.816 | 497 |
| 35.583 | 1199 | 35.123 | 1227 | 35.433 | 1003 | 37.961 | 493 |
| 36.958 | 1084 | 35.741 | 1310 | 36.242 | 1123 | 38.588 | 486 |
| 37.810 | 933 | 36.09 | 1071 | 37.026 | 908 | 39.748 | 483 |
| 38.817 | 840 | 36.901 | 728 | 37.452 | 760 | 41.38 | 2000 |
| 40.589 | 1039 | 38.098 | 794 | 38.844 | 1107 | 42.436 | 857 |
| 41.372 | 1372 | 39.353 | 748 | 39.479 | 876 | 43.004 | 4192 |
| 42.475 | 1130 | 40.098 | 859 | 40.007 | 939 | 44.097 | 4109 |
| 43.001 | 2527 | 40.312 | 896 | 41.379 | 1690 | 44.854 | 1216 |
| 44.092 | 2754 | 41.364 | 1557 | 42.377 | 1017 | 46.225 | 1611 |
| 44.898 | 1214 | 42.445 | 988 | 43.005 | 3041 | 50.107 | 2355 |
| 46.221 | 1470 | 42.997 | 3142 | 44.086 | 3147 | 51.431 | 1359 |
| 47.635 | 822 | 44.101 | 3187 | 44.847 | 1085 | 52.345 | 835 |
| 50.105 | 1587 | 44.842 | 1197 | 46.228 | 1349 | | |
| 51.426 | 1142 | 45.487 | 1029 | 47.127 | 789 | | |
| 52.349 | 819 | 46.218 | 1396 | 50.101 | 1718 | | |
| 56.023 | 547 | 48.074 | 577 | 51.439 | 1116 | | |
| | | 50.099 | 1841 | 52.343 | 861 | | |
| | | 51.439 | 1148 | 54.953 | 469 | | |
| | | 52.346 | 772 | 58.52 | 459 | | |
| | | 54.928 | 526 | | | | |

Starting with PXRD peak locations as displayed in Table 1, the most characteristic peak locations of each polymorph can be selected and grouped by relative intensity to conveniently distinguish the crystalline structure from others.

Such a selection of unique peaks is displayed in Table 2. Thus, for example, the crystalline structure of Form I of Compound A may be identified by the Peak Location Group No. 1, consisting of 4 characteristic PXRD peak locations. Alternatively, the crystalline structure of Form I of Compound A may be identified by the Peak Location Group No. 2, consisting of the 4 characteristic PXRD peak locations of Group No. 1 and an additional 4 peak locations. Alternatively, the Form I crystalline structure of Compound A may be identified by the Peak Location Group No. 3, consisting of the 8 characteristic PXRD peak locations of Group No. 2 and an additional 4 peak locations. This scheme is applied to all four polymorphic forms to identify and distinguish each form from the others.

TABLE 2

Characteristic PXRD Peak Locations for Foms I-IV of Compound A

| Peak Location Group No | Peak Locations (degrees 2θ) | | | |
|---|---|---|---|---|
| | Form I | Form II | Form III | Form IV |
| 1 | 6.612 | 9.328 | 7.748 | 11.46 |
| | 8.832 | 13.774 | 18.349 | 43.004 |
| | 27.024 | 19.78 | 23.198 | 44.097 |
| | 28.134 | 27.305 | 23.851 | 50.107 |
| 2 | 6.612 | 9.328 | 7.748 | 11.46 |
| | 8.832 | 13.145 | 9.632 | 11.848 |
| | 13.268 | 13.774 | 14.07 | 15.643 |
| | 17.696 | 15.79 | 15.383 | 16.957 |
| | 19.492 | 17.872 | 18.349 | 17.524 |
| | 20.003 | 18.748 | 23.198 | 43.004 |
| | 27.024 | 19.78 | 23.851 | 44.097 |
| | 28.134 | 27.305 | 27.841 | 50.107 |

TABLE 2-continued

Characteristic PXRD Peak Locations for Foms I-IV of Compound A

| Peak Location Group No | Peak Locations (degrees 2θ) | | | |
|---|---|---|---|---|
| | Form I | Form II | Form III | Form IV |
| 3 | 6.612 | 8.742 | 7.748 | 8.706 |
| | 8.832 | 9.328 | 9.118 | 11.46 |
| | 13.268 | 13.145 | 9.632 | 11.848 |
| | 17.696 | 13.774 | 14.07 | 15.643 |
| | 17.959 | 15.79 | 15.383 | 16.957 |
| | 19.492 | 17.872 | 18.349 | 17.524 |
| | 20.003 | 18.748 | 18.6 | 19.335 |
| | 20.246 | 19.263 | 18.938 | 21.079 |
| | 21.123 | 19.78 | 19.383 | 26.917 |
| | 26.58 | 20.166 | 23.198 | 43.004 |
| | 27.024 | 26.648 | 23.851 | 44.097 |
| | 28.134 | 27.305 | 27.841 | 50.107 |

Those skilled in the art will recognize that the measurements of the PXRD peak locations for a given crystalline form of the same compound will vary within a margin of error. Such variation can be introduced by differences in sample preparation, instrumentation, or analytical technique, among other factors. Measurements of individual peak locations can vary to a small degree, but an entire peak profile can vary by a greater degree, due to variations in density of packed samples, for example.

Synthese of Polymorphic Forms

Form I:

Compound A Form I is a neutral form with 1:1 molar ratio of hydrate water. It was prepared by crystallizing amorphous neutral Compound A from a mixture of an alcohol and water, in some embodiments, the alcohol is methanol or ethanol. The amorphous Compound A was dissolved in a minimum amount of methanol or ethanol at room temperature. Water was added dropwise until the solution became hazy, whereupon the alcohol was added to make the solution clear. The solution was allowed to stand at room temperature overnight until solid formed. The precipitate was collected by filtration. The PXRD profile of Form I as crystallized from an ethanol/water mixture is displayed in FIG. 1.

Compound A Form I was also prepared by crystallizing amorphous neutral Compound A from commercial grade (non-anhydrous) methanol. The amorphous Compound A was dissolved in a minimum amount of methanol at room temperature and the solution was allowed to stand at room temperature and concentrate via evaporation until solid materials formed. The precipitate was collected by filtration.

Form II:

Compound A Form II is a neutral form with 1:1 molar ratio of hydrate water. It was prepared by mixing Compound A Form I in an organic solvent as a slurry at room temperature. In some embodiments, the organic solvent is methylene chloride or acetone. Conversion to Form II occurs spontaneously. The PXRD profile of Form as crystallized from a slurry of Form I and methylene chloride is displayed in FIG. 2.

Form III:

Compound A Form III is a neutral form with a 1:1 molar ratio of hydrate water. It was prepared by crystallizing Compound A amorphous neutral form from a mixture of an organic solvent and water at elevated temperature. Preferably, the organic solvent is n-propanol. The procedure is described below:

About 6 g of amorphous, unmicronized Compound A solid was dissolved in 45 mL n-propanol by warming in a heating mantle under a nitrogen atmosphere. About 80 mL of water was added portion-wise until precipitation was detected. Another 20 mL of n-propanol was added to the slurry and the mixture was heated to 70° C. The heating mantle was removed and a precipitate formed. The slurry was stirred overnight and filtered and washed with 4:1 $H_2O$/n-propanol. The solid was dried in vacuo at 40° C. The PXRD profile of Form III as crystallized from amorphous, unmicronized Compound A and a mixture of n-propanol/water is displayed in FIG. 3.

Form IV:

Compound A Form IV is a neutral form with a 1:1 molar ratio of hydrate water. It was prepared by mixing Compound A Form I in either acetonitrile or n-propanol as a slurry at room temperature. Conversion to Form IV occurs spontaneously. in large scale, it was prepared by the procedure described below:

To a 5 Liter, three-necked round bottom flask equipped with a mechanical stirrer, thermocouple, and reflux condenser, was charged 200 g of Compound A neutral form monohydrate, 2.2 L of n-propanol and 2.0 L of water. The suspension was agitated and heated up to 70° C. to dissolve all solids. The solution was then cooled to 60° C. and Form IV seeds were charged (about 0.5 g). The mixture was stirred at a temperature between 58 and 60° C. for 4 hours while allowing the product to precipitate. The mixture was then cooled to 50° C. over one hour and agitated at this temperature over night. The batch was further cooled to a temperature between 5 and 10° C. over three hours. The product was collected by filtration and dried in a vacuum oven at 50° C. for 10 hours. The recovery was 180.4 g (90.2%). The PXRD analysis is displayed in FIG. 4 and shows pure Form IV crystals.

In the above procedures for the preparation of Forms III and IV, the form of Compound A used as the starting material can alternately be amorphous, Forms I-IV, or any combination thereof.

Polymorph Purity

Preferably, the crystalline polymorphs Forms I-IV of the monohydrate of Compound A are substantially free of chemical impurities (e.g., by-products generated during the preparation of the polymorphs) and of other polymorphic crystalline forms. "Substantially free" of chemical impurities for the purposes of this invention means less than or equal to about 5% w/w of chemical impurities, preferably, less than or equal to about 3% w/w of chemical impurities, more preferably, less than or equal to about 2% w/w of chemical impurities, and even more preferably, less than or equal to about 1% w/w of chemical impurities. The term "purified" or "in purified form" for a polymorph refers to the physical state of said polymorph after being obtained from a purification process or processes described herein or well known to the skilled artisan, in sufficient purity to be characterizable by standard analytical techniques described herein or well known to the skilled artisan. Purified forms of the crystalline polymorph Forms I-IV of the monohydrate of Compound A are substantially free of chemical impurities.

Pharmaceutical Compositions

For preparing pharmaceutical compositions from the polymorphs described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The inventive polymorphs may also be deliverable transdermally. The transdermal composition can take the form of creams, lotions, aerosols and/or emulsions and can be included in a transdermal patch of the matrix or reservoir type as are conventional in the art for this purpose.

In some embodiments, the inventive polymorph is administered orally.

In some embodiments, the pharmaceutical preparation is in a unit dosage form. In such form, the preparation is subdivided into suitably sized unit doses containing appropriate quantities of the active component, e.g., an effective amount to achieve the desired purpose.

Dosages

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 my to about 250 mg, according to the particular application.

The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in one to four divided doses.

Co-Formulations

In some embodiments of the treatment of cancer, at least one of the polymorphs disclosed herein is administered in combination with one of the following antineoplastic agents: gemcitabine, paclitaxel (Taxol®), 5-Fluorourcil (5-FU), cyclophosphamide (Cytoxan®), temozolomide, or Vincristine.

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol® and is described in more detail below in the subsection entitled "Microtubule Affecting Agents"), Mithramycin, Deoxyco-formycin, Mitomycin-C, L-Asparaginase, Interferons (especially IFN-a), Etoposide, and Teniposide.

Hormones and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 2002 edition (Medical Economics Company, Montvale, N.J. 07645-1742, USA); the disclosure of which is incorporated herein by reference thereto.

In another embodiment, the present invention provides a method of treating cancer, comprising administering, concurrently or sequentially, an effective amount of at least one of the polymorphs disclosed herein and a microtubule affecting agent e.g., paclitaxel.

Another embodiment of the invention is directed to a method treating cancer, comprising administering to a patient in need thereof concurrently or sequentially, a therapeutically effective amount of (a) at least one of the polymorphs disclosed herein, and (b) an antineoplastic agent, microtubule affecting agent or anti-angiogenesis agent.

As used herein, a microtubule affecting agent is a compound that interferes with cellular mitosis, i.e., having an anti-mitotic effect, by affecting microtubule formation and/or action. Such agents can be, for instance, microtubule stabilizing agents or agents that disrupt microtubule formation.

Microtubule affecting agents useful in the invention are well known to those of skill in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) *Science,* 274:2009) estramustine, nocodazole, MAP4, and the like. Examples of such agents are also described in the scientific and patent literature, see, e.g., Bulinski (1997) *J. Cell Sci.* 110:3055-3064; Panda (1997) *Proc. Natl. Acad. Sci.* USA 94:10560-10564; Muhlradt (1997) Cancer Res. 57:3344-3346; Nicolaou (1997) *Nature* 387:268-272; Vasquez (1997) *Mol. Biol. Cell.* 8:973-985; Panda (1996) *J. Biol. Chem.* 271:29807-29812.

In some embodiments, the agents are compounds with paclitaxel-like activity. These include, but are not limited to paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) *Oncology,* 6: 17-23, Horwitz (1992) *Trends Pharmacol Sci.* 13: 134-146, Rowinsky (1990) *J. Natl. Canc. Inst.* 82:1247-1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) *Cancer Chemoter. Pharmacol.* 41:37-47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

Compounds with possible tubulin polymerization activity can be screened in vitro. In a preferred embodiment, the compounds are screened against cultured WR21 cells (derived from line 69-2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) *Lab. Anim. Sci.*, 45(2):145-150.

Other methods of screening compounds for desired activity are well known to those of skill in the art. Typically such assays involve assays for inhibition of microtubule assembly and/or disassembly. Assays for microtubule assembly are described, for example, by Gaskin et al. (1974) *J. Molec. Bol.*, 89: 737-758. U.S. Pat. No. 5,569,720 also provides in vitro and in vivo assays for compounds with paclitaxel-like activity.

Methods for the safe and effective administration of the above-mentioned microtubule affecting agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montale, N.J. 07645-1742, USA); the disclosure of which is incorporated herein by reference thereto.

The amount and frequency of administration of the inventive polymorphs and the chemotherapeutic agents and/or radiation therapy will be regulated according to the judgment of the attending clinician (physician) considering such factors as age, condition and size of the patient as well as severity of the disease being treated. A dosage regimen of the inventive polymorphs can be oral administration of from 10 mg to 2000 mg/day, preferably 10 to 1000 mg/day, more preferably 50 to 600 mg/day, in two to four (preferably two) divided doses, to block tumor growth. Intermittent therapy (e.g., one week out of three weeks or three out of four weeks) may also be used.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

In the methods of this invention, the inventive polymorph is administered concurrently or sequentially with a chemotherapeutic agent and/or radiation. Thus, it is not necessary that, for example, the chemotherapeutic agent and the inventive polymorph, or the radiation and the inventive polymorph, should be administered simultaneously or essentially simultaneously. The advantage of a simultaneous or essentially simultaneous administration is well within the determination of the skilled clinician.

Also, in general, the inventive polymorph and the chemotherapeutic agent do not have to be administered in the same pharmaceutical composition, and may, because of different physical and chemical characteristics, have to be administered by different routes. For example, the inventive polymorph may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of an inventive polymorph, and chemo-therapeutic agent and/or radiation will depend upon the diagnosis of the attending physicians and their judgment of the condition of the patient and the appropriate treatment protocol.

The inventive polymorph, and chemotherapeutic agent and/or radiation may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with the inventive polymorph.

If the inventive polymorph, and the chemotherapeutic agent and/or radiation are not administered simultaneously or essentially simultaneously, then the initial order of administration of the inventive polymorph, and the chemotherapeutic agent and/or radiation, may not be important. Thus, the inventive polymorph may be administered first, followed by the administration of the chemotherapeutic agent and/or radiation, or the chemotherapeutic agent and/or radiation may be administered first, followed by the administration of the inventive polymorph. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient.

For example, the chemotherapeutic agent and/or radiation may be administered first, especially if it is a cytotoxic agent, and then the treatment continued with the administration of the inventive polymorph followed, where determined advantageous, by the administration of the chemotherapeutic agent and/or radiation, and so on until the treatment protocol is complete.

The inventive polymorphs may also be useful in the treatment of pain associated with a chemokine mediated disease. Such pain can be described by or associated with the following: acute inflammatory pain, chronic inflammatory pain, acute neuropoathic pain, chronic neuropathic pain, acute inflammation, rheumatoid arthritis, psoriasis, atopic dermatitis, asthma, COPD, adult respiratory disease, arthritis, inflammatory bowel disease, Crohn's disease, ulcerative colitis, septic shock, endotoxic shock, gram negative sepsis, toxic shock syndrome, stroke, cardiac and renal reperfusion injury, glomerulonephritis, thrombosis, Alzheimer's disease, graft vs. host reaction, allograft rejections, malaria, acute respiratory distress syndrome, delayed type hypersensitivity reaction, atherosclerosis, cerebral and cardiac ischemia, osteoarthritis, multiple sclerosis, restinosis, angiogenesis, osteoporosis, gingivitis, respiratory viruses, herpes viruses, hepatitis viruses, HIV, Kaposi's sarcoma associated virus, meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute and chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred and corneal neovascularization, polymyositis, vasculitis, acne, gastric and duodenal ulcers, celiac disease, esophagitis, glossitis, airflow obstruction, airway hyperresponsiveness, bronchiectasis, bronchiolitis, bronchiolitis obliterans, chronic bronchitis, cor pulmonae, cough, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy, periodontitis, transplant reperfusion injury and early transplantation rejection, and chronic inflammation.

This invention also provides a method of treating a CXCR1 and/or a CXCR2 mediated disease or condition selected from the group consisting of pain (e.g., acute pain, acute inflammatory pain, chronic inflammatory pain, and neuropathic pain), acute inflammation, chronic inflammation, rheumatoid arthritis, psoriasis, atopic dermatitis, asthma, COPD, adult respiratory disease, arthritis, inflammatory bowel disease, Crohn's disease, ulcerative colitis, septic shock, endotoxic shock, gram negative sepsis, toxic shock syndrome, stroke, ischemia reperfusion injury, renal reperfusion injury, glomerulonephritis, thrombosis, Alzheimer's disease, graft vs. host reaction (i.e., graft vs. host disease), allograft rejections (e.g., acute allograft rejection, and chronic allograft rejection), malaria, acute respiratory distress syndrome, delayed type hypersensitivity reaction, atherosclerosis, cerebral ischemia, cardiac ischemia, osteoarthritis, multiple sclerosis, restinosis, angiogenesis, osteoporosis, gingivitis, respiratory viruses, herpes viruses, hepatitis viruses, HIV, Kaposi's sarcoma associated virus (i.e., Kaposi's sarcoma), meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute pancreatitis, chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred, corneal neovascularization, polymyositis, vasculitis, acne, gastric ulcers, duodenal ulcers, celiac disease, esophagitis, glossitis, airflow obstruction, airway hyperresponsiveness (i.e., airway hyperreactivity), bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy (i.e., the treatment of burns), periodontitis, cancer, transplant reperfusion injury, early transplantation rejection (e.g., acute allograft rejection) in a patient in need of such treatment comprising administering to said patient an effective amount of at least one of the inventive polymorphs.

This invention also provides a method of treating a CCR7 mediated disease or condition selected from the group consisting of: pain (e.g., acute pain, acute inflammatory pain, chronic inflammatory pain, and neuropathic pain), acute inflammation, chronic inflammation, acute allograft rejection, acute respiratory distress syndrome, adult respiratory disease, airway hyperreactivity, allergic contact dermatitis, allergic rhinitis, alopecia areata, alzheimer's disease, angiogenic ocular disease, antiphospholipid syndromes, aplastic anemia, asthma, atherosclerosis, atopic dermatitis, autoimmune deafness (including, for example, Meniere's disease), autoimmune hemolytic syndromes, autoimmune hepatitis, autoimmune neuropathy, autoimmune ovarian failure, autoimmune orchitis, autoimmune thrombocytopenia, bronchiolitis, bronchiolitis obliterans syndrome, bullous pemphigoid, burn therapy (i.e., the treatment of burns), cancer, cerebral ischemia, cardiac ischemia, chronic allograft rejection, chronic allograft vasculopathy, chronic bronchitis, chronic inflammatory demyelinating polyneuropathy, chronic sinusitis, cirrhosis, CNS vasculitis, COPD, Cor pneumoniae, Crohn's disease, cryoglobulinemia, crystal-induced arthritis, delayed-type hypersensitivity reactions, dermatomyositis, diabetes, diabetic retinopathy, drug-induced autoimmunity, dyspnea, emphysema, epidermolysis bullosa acquisita, endometriosis, fibrotic diseases, gastritis, glomerulonephritis, Goodpasture's syndrome, graft vs host disease, Graves' disease, Gullain-Barre disease, Hashimoto's thyroiditis, hepatitis-associated autoimmunity, HIV-related autoimmune syndromes and hematologic disorders, hyperoxia-induced inflammation, hypercapnea, hyperinflation, hypophytis, hypoxia, idiopathic thrombocytic pupura, inflammatory bowel diseases, interstitial cystitis, interstitial pneumonitis, juvenile arthritis, Langerhans' cell histiocytitis, lichen planus, metal-induced autoimmunity, multiple sclerosis, myasthenia gravis, myelodysplastic syndromes, myocarditis including viral myocarditis, myositis, neuropathies (including, for example, IgA neuropathy, membranous neuropathy and idiopathic neuropathy), nephritic syndrome, ocular inflammation, optic neuritis, osteoarthritis, pancreatitis, paroxysmal nocturnal hemoglobutinemia, pemphigus, polymyalgia, polymyositis, post-infectious autoimmunity, pulmonary fibrosis, primary biliary cirrhosis, psoriasis, pruritis, rheumatoid arthritis, reactive arthritis, ankylosing spondylitis, psoriatic arthritis, Raynaud's phenomenon, Reiter's syndrome, ischemia injury, restenosis, sarcoidosis, scleritis, scleroderma, secondary hematologic manifestation of autoimmune diseases (such as, for example, anemias), silicone implant associated autoimmune disease, Sjogren's syndrome, systemic lupus erythematosus, thrombocytopenia, thrombosis, transverse myelitis, tubulointerstitial nephritis, ulcerative colitis, uveitis, vasculitis and vasculitis syndromes (such as, for example, giant cell arteritis, Behcet's disease and Wegeners granulomatosis), and vitiligo in a patient in need of such treatment comprising administering to said patient an effective amount of at least one inventive polymorph.

This invention also provides a method of treating a chemokine mediated disease or condition in a patient in need of such treatment comprising administering to said patient at least one (usually 1) inventive polymorph, in combination with at least one (usually 1) other medicament (e.g., a drug, agent or therapeutic) selected from the group consisting of:
   a) disease modifying antirheumatic drugs;
   b) nonsteroidal anitinflammatory drugs;
   c) COX-2 selective inhibitors;
   d) COX-1 inhibitors;
   e) immunosuppressives;
   f) steroids;
   g) biological response modifiers; and
   h) other anti-inflammatory agents or therapeutics useful for the treatment of chemokine mediated diseases.

The above-listed medicaments can be used in conjunction with at least one inventive polymorph in the treatment of pain.

This invention also provides a method of treating a pulmonary disease (e.g., COPD, asthma or cystic fibrosis) in a patient in need of such treatment comprising administering to said patient a therapeutically effective amount of at least one inventive polymorph in combination with at least one (usually 1) compound selected from the group consisting of: glucocorticoids, 5-lipoxygenase inhibitors, β-2 adrenoceptor agonists, muscarinic M1 antagonists, muscarinic M3 antagonists, muscarinic M2 agonists, NK3 antagonists, LTB4 antagonists, cysteinyl leukotriene antagonists, bronchodilators, PDE4 inhibitors, PDE inhibitors, elastase inhibitors, MMP inhibitors, phospholipase A2 inhibitors, phospholipase D inhibitors, histamine H1 antagonists, histamine H3 antagonists, dopamine agonists, adenosine A2 agonists, NK1 and NK2 antagonists, GABA-b agonists, nociceptin agonists, expectorants, mucolytic agents, decongestants, antioxidants, anti-IL-8 anti-bodies, anti-IL-5 antibodies, anti-IgE antibodies, anti-TNF antibodies, IL-10, adhesion molecule inhibitors, and growth hormones.

This invention also provides a method of treating multiple sclerosis in a patient in need of such treatment comprising administering to said patient, a therapeutically effective amount of at least one (usually 1) inventive polymorph, in combination with at least one compound selected from the group consisting of glatiramer acetate, glucocorticoids, methotrexate, azothioprine, mitoxantrone, chemokine inhibitors, and CB2-selective agents.

This invention also provides a method of treating multiple sclerosis in a patient in need of such treatment comprising administering to said patient a therapeutically effective amount of at least one (usually 1) inventive polymorph, in combination with at least one compound selected from the group consisting of: methotrexate, cyclosporin, leflunimide, sulfasalazine, β-methasone, β-interferon, glatiramer acetate, and prednisone.

This invention also provides a method of treating rheumatoid arthritis in a patient in need of such treatment comprising administering to said patient a therapeutically effective amount of at least one (usually one) inventive polymorph.

Alternatively, such treatment may further comprise administering to said patient a therapeutically effective amount of at least one compound selected from the group consisting of COX-2 inhibitors, COX inhibitors, immunosuppressives (e.g., methotrexate, cyclosporin, leflunimide and sulfasalazine), steroids (e.g., betamethasone, cortisone and dexamethasone), PDE IV inhibitors, anti-TNF-α compounds, MMP inhibitors, glucocorticoids, chemokine inhibitors, CB2-selective inhibitors, and other classes of compounds indicated for the treatment of rheumatoid arthritis.

This invention also provides a method of treating stroke and ischemia reperfusion injury in a patient in need of such treatment comprising administering to said patient a therapeutically effective amount of at least one inventive polymorph in combination with at least one compound selected from the group consisting of thrombolitics (e.g., tenecteplase, TPA, alteplase), antiplatelet agents (e.g., gpII/IIIa), antagonists (e.g., abciximab and eftiifbatide), anticoagulants (e.g., heparin), and other compounds indicated for the treatment of rheumatoid arthritis.

This invention also provides a method of treating psoriasis in a patient in need of such treatment comprising administering to said patient a thereapeutically effective amount of at least one (usually 1) inventive polmorph, in combination with at least one compound selected from the group consisting of immunosuppressives (e.g., methotrexate, cyclosporin, leflunimide and sulfasalazine), steroids (e.g., β-methasone) and anti-TNF-α compounds (e.g., etonercept and infliximab).

This invention also provides a method of treating COPD in a patient in need of such treatment comprising administering to said patient a therapeutically effective amount of at least one (usually one) inventive polymorph.

This invention also provides a method of treating arthritis in a patient in need of such treatment comprising administering to said patient a therapeutically effective amount of at least one (usually one) inventive polymorph.

This invention also provides a method of treating osteoarthritis in a patient in need of such treatment comprising administering to said patient a therapeutically effective amount of at least one (usually one) inventive polymorph.

In accordance with experience and knowledge, the practicing physician can modify each protocol for the administration of a component (therapeutic agent—i.e., the inventive polymorph, chemotherapeutic agent or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radio-logical studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Other than as shown in the operating examples or as otherwise indicated, all numbers used in the specification and claims expressing quantities of ingredients, reaction conditions, and so forth, are understood as being modified in all instances by the term "about." The above description is not intended to detail all modifications and variations of the invention. It will be appreciated by those skilled in the art that changes can be made to the embodiments described above without departing from the inventive concept. It is understood, therefore, that the invention is not limited to the particular embodiments described above, but is intended to cover modifications that are within the spirit and scope of the invention, as defined by the language of the following claims.

What is claimed is:

1. A crystalline Form IV of a monohydrate of Compound A of the formula:

that exhibits a powder x-ray diffraction pattern as shown in FIG. 4.

2. A process for preparing the crystalline Form IV of claim 1 from Compound A comprising the step of mixing Compound A with acetonitrile as a slurry at room temperature until Form IV crystals precipitate.

3. A process for preparing the crystalline Form IV of claim 1 from Compound A comprising the steps of:
a) mixing Compound A with a first mixture of n-propanol and water to form a second mixture;
b) agitating said second mixture while heating to about 70° C. until substantially all solids are dissolved;
c) cooling said second mixture to about 60° C.; and
d) agitating said second mixture until Form IV crystals precipitate.

4. The process of claim 3 wherein the first mixture comprises n-propanol and water in a ratio of about 1.1:1.

5. A capsule comprising a crystalline Form IV of claim 1, and at least one pharmaceutically acceptable excipient or carrier.

* * * * *